United States Patent [19]

Daniel et al.

[11] 4,299,980

[45] Nov. 10, 1981

[54] CATALYTIC OXYDEHYDROGENATION PROCESS

[75] Inventors: Chelliah Daniel; Phyllis L. Brusky, both of Columbus, Ohio

[73] Assignee: Ashland Oil, Inc., Ashland, Ky.

[21] Appl. No.: 126,581

[22] Filed: Mar. 3, 1980

[51] Int. Cl.³ .................... C07C 51/377; C07C 57/05; C07C 67/317; C07C 69/54
[52] U.S. Cl. ................................. 562/599; 252/435; 252/437; 560/214
[58] Field of Search ....................... 562/599; 560/214; 252/437, 435; 260/405.5

[56] References Cited

U.S. PATENT DOCUMENTS

| | | | |
|---|---|---|---|
| 3,948,959 | 4/1976 | Caraterra et al. | 562/599 |
| 4,029,695 | 6/1977 | Watkins | 562/599 |
| 4,081,465 | 3/1978 | Gruber et al. | 562/599 |

*Primary Examiner*—Vivian Garner
*Attorney, Agent, or Firm*—William Kammerer

[57] ABSTRACT

Isobutyric acid or a functional equivalent, e.g., a lower alkyl ester is oxidatively dehydrogenated to effect the vapor phase conversion thereof to the corresponding $\alpha,\beta$-ethylenically unsaturated derivative by contact with a heterogeneous catalyst in the presence of molecular oxygen. The catalyst is composed of calcined phosphates of iron containing tellurium as a modifier or dopant component.

3 Claims, No Drawings

CATALYTIC OXYDEHYDROGENATION PROCESS

BACKGROUND OF THE INVENTION

1. Field of the Invention

This invention relates to a process for the conversion of isobutyric acid to methacrylic acid including the like conversion of a lower alkyl ester of isobutyric acid.

2. Description of the Prior Art

There is considerable prior art directed to the oxydehydrogenation of the lower saturated mono-carboxylic acids to prepare the corresponding $\alpha,\beta$-ethylenically unsaturated acids. The initial work reported in this area was that of thermally effecting the indicated oxydehydrogenation by the vapor phase reaction of the acid substrate with iodine and oxygen. This approach has not attracted much attention as a potentially viable way for commercially implementing the underlying reaction. This is understandably so inasmuch as iodine is costly, exhibits extreme corrosivity properties and poses considerable problems in realizing complete recovery of the comparatively large amounts thereof required in the process.

As the subsequent prior art picture amply points up, the heterogeneous catalytic method for effecting the oxydehydrogenation reaction is viewed as being much more attractive from the standpoint of potential commercial applicability. In the main, the more recent relevant prior art activities have centered on the use of two types of catalyst compositions for this purpose. One type includes generally the heteropoly-acids, typically representative of which 12-molybdophosphate optionally including vanadium and/or tungsten elements in a like structural arrangement. The other type catalyst includes those systems having in common a calcined iron phosphate matrix.

Iron phosphate subjected to calcination exists in a plurality of crystalline phases or species. While it is believed that the oxidation/reduction coupled involved in the underlying reaction is attributable to the iron phosphate, which species is or are catalytically active has not been identified. There is, however, evidence that the presence of an extrinsic metal component in the preparation serves to facilitate the formation of the catalytically active species. For example, U.S. Pat. No. 3,948,959 notably teaches that an alkali or alkaline earth metal as the extrinsic metal component is effective for this purpose. The present invention accordingly represents a furtherance of this particular aspect of the current state of the art.

SUMMARY OF THE INVENTION

In accordance with this invention, a catalytic process is provided for effecting the oxidative dehydrogenation of isobutyric acid or a lower alkyl ester thereof to form the corresponding $\alpha,\beta$-ethylenically unsaturated derivative. The process of this invention comprises contacting a heterogeneous catalyst at a temperature from 300–500° C. with a co-feed of said substrate and diluted oxygen gas, characterized in that said catalyst is calcined iron phosphate containing tellurium as the modifier or dopant component. In the broadest aspect of the invention the contemplated catalyst is defined by the gram-atom empirical formula $FeP_{1-2}Te_{0.01-1}O_x$ in which x represents the number of oxygen atoms bound to the other metals in their respective states of oxidation in the catalyst.

DESCRIPTION OF THE PREFERRED EMBODIMENTS

There are a number of techniques applicable for preparing the catalyst useful in the practice of this invention. Of these, the more facile methods involve preparing the integral composition prior to calcination. This can be readily accomplished by employing the so-called slurry method or the precipitation method. In the latter method an aqueous solution of phosphoric acid and applicable compounds of iron and tellurium is first prepared and thereupon neutralized with an appropriate base in order to precipitate the solute principally as iron phosphate. The precipitate is desirably carefully washed to remove all traces of water solubles and then dried prior to calcining. In the alternative, one can add ammonium phosphate to the solution of the indicated compounds in order to effect precipitation. Any water-soluble salt of iron can be used. However, because of the solubility characteristics of the nitrate salt, among other reasons, said compound is preferred. Tellurium dioxide is particularly representative of a suitable tellurium compound.

The so-called slurry method is even more convenient to carry out and for this reason represents the preferred method herein. In accordance with this procedure, the aqueous solution of the iron and tellurium compounds together with the phosphoric acid is obtained as previously noted. However, no precipitation is effected as the solution is subjected to heating with stirring in order to remove water. Heating is continued until the mass can be no longer stirred. The residue is then fragmented and again heated at a moderately elevated temperature in the order of about 120° C. until completely dried. Thereupon the dried composite is sized and calcined. Suitable calcination temperatures broadly range from 400°–450° C. Applicable calcination periods range from 2–16 hours.

In the manner of either of these techniques, a supported catalyst can be prepared. For example, in the slurry method colloidal silica or any other form thereof as well as other supports such as alumina, quartz, titanium dioxide, etc., can be added prior to removing the water content. Similarly, in the alternate method described, the precipitation of the indicated compounds can be accomplished in the presence of suspended particulates of the intended support.

The catalyst compositions of this invention can be employed in a fluidized, stirred tank reactor, or fixed-bed type reactor. Because of the convenience associated with the use of a fixed-bed reactor in a small scale operation, such a reactor will be exemplified herein. In the preferred mode of operation the feed to the reactor comprises a pre-heated gaseous mixture of the substrate, molecular oxygen, steam and inert diluent gas. A pre-heat temperature in the range of about 300° to 350° C. is customarily observed. A broad range of applicable reaction temperatures is from 300°–500° C. but more generally a temperature of from 375° to 425° C. provides for optimum processing.

The mole ratio of molecular oxygen to substrate is from 0.5 to 1.5 and more preferably from 0.7 to 0.75 in the case where the substrate is isobutyric acid per se. While steam is not necessary for the purpose of effecting the reaction, the presence thereof in the feed is particularly desirable insofar as it acts as a heat sink and in such a capacity serves to minimize combustion of the substrate. An applicable mole ratio of water to the substrate in the feed is from about 8-20. Optimum ratio is more in the order of from 12 to 15.

Another important parameter resides in the concentration of the substrate in the feed. Expressed in terms of mole percents, the concentration of the contemplated substrates ranges broadly from 0.1-20. As is common in reactions of this type, yield of the desired product is an inverse function of the concentration. From the standpoint of achieving a reasonable through-put combined with an acceptable yield, the concentration of the substrate in the feed is from about 3-6 mole percent. Concentration is controlled by the amount of the inert gas present in the feed stream. The preferred diluent gas is nitrogen although other gases such as carbon dioxide, helium, argon, and the like are suitable. Of course if the desired concentration of substrate permits, air represents a suitable diluted oxidant.

A further important parameter is that of contact time. Contact or reaction time is defined as the catalyst volume divided by the volume of gas feed per second at reaction temperature. The catalyst volume is the bulk volume occupied by the catalyst in the reactor. The term catalyst in this sense not only includes the modified iron phosphate itself but also the support if present. Accordingly, applicable reaction times range from 0.05-3.0 seconds and more generally in the order of from 0.1-1.0 second. The reaction is carried out preferably at atmospheric pressure although a higher pressure up to about 10 atmospheres is applicable.

EXAMPLE II

This example illustrates the use of the catalyst composition of Example I in effecting the oxidative dehydrogenation of isobutyric acid. The reactor and the general manner of conducting the reaction were the same for each of the enumerated runs. The procedure observed consisted of feeding a pre-heated mixture of the isobutyric acid, oxygen, nitrogen and steam through a stainless steel tube of $\frac{1}{2}''$ OD ($\frac{3}{8}''$ ID) and approximately 18" in length containing the test catalyst as a 15 cc. packed bed (7.5 cc. supported catalyst+7.5 cc. quartz packing) maintained at the reaction temperature utilized in the particular run.

The pre-heater consisted of a length of stainless steel tube similar to the reactor but packed with glass beads. Any carbon dioxide formed in the course of reaction was absorbed in an Ascarite tube protected by a calcium sulfate absorber for any uncondensed water. The condensed organic product was separated from the water, collected and analyzed by the internal standard method of gas chromotography.

Other pertinent processing conditions observed for the individual runs are set forth in Table 1 presented hereinbelow. The results obtained in terms of selectivity and conversion are likewise given in said table. Conversion represents the mole ratio of substrate consumed to that charged to the reactor. Selectivity to methacrylic acid represents the mole ratio of methacrylic acid found in the effluent to that of IBA consumed in the reaction.

TABLE 1

| RUN NO. | REACTION TEMP. (°C.) | REACTION TIME (Sec.) | OXYDEHYDROGENATION OF ISOBUTYRIC ACID (IBA) CHARGE TO REACTOR | | | | TOTAL GAS FEED (l/hr) | CONVERSION (%) | SELECTIVITY (%) | IBA YIELD % |
|---|---|---|---|---|---|---|---|---|---|---|
| | | | $O_2$/IBA (Mole Ratio) | IBA Conc. (Mole %) | IBA FEED (gm/hr @ RT) | WATER (gm/hr @ RT) | | | | |
| 1 | 390 | 0.29 | 0.68 | 5.5 | 11.0 | 20 | 41.9 | 87.5 | 68.2 | 59.7 |
| 2 | 395 | 0.29 | 0.70 | 5.5 | 11.0 | 20 | 41.8 | 86.4 | 69.7 | 60.7 |
| 3 | 400 | 0.26 | 0.70 | 5.0 | 11.0 | 20 | 42.5 | 77.1 | 70.5 | 54.0 |

EXAMPLE I

The purpose of this example is to illustrate the hereinabove described slurry method for preparing a supported catalyst useful in the practice of this invention. Iron nitrate nonahydrate in the amount of 404.4 g. along with 8.02 g. of tellurium dioxide and 127.16 g. of 85% phosphoric acid were dissolved in 400 ml. of distilled water. One hundred milliliters of silica gel containing 40% $SiO_2$ were added to the resultant solution. The solution was then stirred at 85° C. until the bulk of the water had been evaporated. The resultant paste was further dried at 120° C. until in condition to be fragmented whereupon drying was continued for 12 hours. The dried mixture was calcined at 450° C. for 6 hours. The gram-atom empirical formula of the calcined composition follows: $FeP_{1.3}Te_{0.05}O_x$.

We claim:

1. In a process for the catalytic conversion of isobutyric acid or a lower alkyl ester thereof to the corresponding $\alpha,\beta$-ethylenically unsaturated derivative via thee oxydehydrogenation reaction wherein an iron phosphate catalyst is contacted with a gaseous feed stream containing said acid or ester substrate and oxygen at a temperature between about 300° and 500° C., the improvement of effecting said oxydehydrogenation reaction in the presence of a modified iron phosphate catalyst having the gram-atom empirical formula $FeP_{1.2}Te_{0.01-1}O_x$ in which x represents the number of oxygen atoms bound to the other elements in their respective states of oxidation in the catalyst.

2. The process in accordance with claim 1 wherein the substrate is isobutyric acid.

3. The process in accordance with claim 2 wherein the modified iron phosphate catalyst has the gram-atom formula $FeP_{1.3}Te_{0.05}O_x$.

* * * * *